United States Patent
Fujimura et al.

(10) Patent No.: US 6,821,361 B2
(45) Date of Patent: Nov. 23, 2004

(54) QUANTITATIVE MEASURING METHOD AND APPARATUS OF METAL PHASE USING X-RAY DIFFRACTION METHOD, AND METHOD FOR MAKING PLATED STEEL SHEET USING THEM

(75) Inventors: Toru Fujimura, Chiba (JP); Akira Yamamoto, Chiba (JP)

(73) Assignee: JFE Steel Corporation, Tokyo (JP)

( * ) Notice: Subject to any disclaimer, the term of this patent is extended or adjusted under 35 U.S.C. 154(b) by 0 days.

(21) Appl. No.: 10/130,711

(22) PCT Filed: Sep. 18, 2001

(86) PCT No.: PCT/JP01/08093

§ 371 (c)(1),
(2), (4) Date: May 22, 2002

(87) PCT Pub. No.: WO02/25257

PCT Pub. Date: Mar. 28, 2002

(65) Prior Publication Data
US 2002/0174918 A1 Nov. 28, 2002

(30) Foreign Application Priority Data

Sep. 22, 2000 (JP) ........................................ 2000-288228
Sep. 27, 2000 (JP) ........................................ 2000-293792
Nov. 30, 2000 (JP) ........................................ 2000-364965

(51) Int. Cl.$^7$ .............................................. G01N 23/20
(52) U.S. Cl. ........................ 148/508; 148/533; 378/73
(58) Field of Search ................................. 148/508, 533; 266/78; 378/71, 73, 84

(56) References Cited

U.S. PATENT DOCUMENTS

| | | | | |
|---|---|---|---|---|
| 4,064,437 A | * | 12/1977 | Hirose et al. | 250/273 |
| 4,649,556 A | * | 3/1987 | Rinik et al. | 378/71 |
| 4,764,945 A | * | 8/1988 | Abe | 378/50 |
| 5,155,751 A | * | 10/1992 | Chohata et al. | 378/71 |
| 5,414,747 A | * | 5/1995 | Ruud et al. | 378/73 |
| 6,307,917 B1 | * | 10/2001 | Shimizu et al. | 378/145 |
| 6,529,578 B1 | * | 3/2003 | Taguchi et al. | 378/84 |

FOREIGN PATENT DOCUMENTS

| | | | |
|---|---|---|---|
| EP | 0348574 | * | 1/1990 |
| JP | 51-108884 | | 9/1976 |
| JP | 52-20320 | | 2/1977 |
| JP | 56-143949 | | 11/1981 |
| JP | 2-253144 | | 10/1990 |
| JP | 6-347247 | | 12/1994 |
| JP | 2000-147200 | | 5/2000 |

OTHER PUBLICATIONS

ASM Materials Engineering Dictionary, Davis, J.R. ed., ASM International, 1992, p. 110.*

* cited by examiner

*Primary Examiner*—George Wyszomierski
(74) *Attorney, Agent, or Firm*—Young & Thompson

(57) ABSTRACT

A method and apparatus for quantitatively measuring a metal phase contained in a galvanized layer by X-ray diffractometry, and a method of producing a galvanized steel sheet by using the method and apparatus. The diffracted X-ray intensity from a metal phase contained in the galvanized layer is increased to improve measurement accuracy, thereby permitting application to on-line measurement. The diffracted X-rays from the metal phase are measured over a predetermined range on a Debye ring, or measured at a plurality of positions on the Debye ring to increase the diffracted X-ray intensity, thereby improving measurement accuracy. The X-ray beam produced by an X-ray source is compressed and made parallel and monochromatic by a multilayer film mirror to increase diffracted X-ray intensity, improving measurement accuracy. Particularly, the present invention is applied to measurement of the degree of alloying of hot-dip galvanization.

8 Claims, 4 Drawing Sheets

QUANTITATIVE MEASURING METHOD AND APPARATUS OF METAL PHASE USING X-RAY DIFFRACTION METHOD, AND METHOD FOR MAKING PLATED STEEL SHEET USING THEM

TECHNICAL FIELD

The present invention relates to a method and apparatus for quantitatively measuring a metal phase by X-ray diffractometry, and a method of producing a galvanized steel sheet by using the method and apparatus. Particularly, the present invention relates to a method and apparatus for accurately measuring the deposit amount of a metal phase contained in a galvanized layer, particularly a desired metal phase of not less than two metal phases contained a galvanized layer, in a nondestructive state, and a method of producing a galvanized steel sheet by using the method and apparatus.

BACKGROUND ART

The quality characteristics (pealing resistance in processing, corrosion resistance, and the like) of a plating containing alloy phases significantly vary depending upon the deposit amount of each of the alloy phases in a galvanized layer. Therefore, in order to produce a plated product of high quality, it is important to accurately measure the deposit amount of each of the phases and control production conditions such as heat treatment conditions, and the like.

A typical example of plated products having galvanized layers containing alloy phases is an alloyed hot-dip galvanized steel sheet comprising a galvanized layer containing several types of Fe—Zn alloy phases. The alloyed hot-dip galvanized steel sheet is produced by heat-treating a hot-dip galvanized steel sheet to positively grow the Fe—Zn alloy phases in the galvanized layer in order to improve the quality characteristics such as pealing resistance, weldability, corrosion resistance and adhesion of a coated film after coating, and the like. The Fe—Zn alloy phases of the galvanized layer on the steel sheet contain a $\delta_1$ phase as a main phase, and small amounts of $\Gamma$ phase and $\zeta$ phase depending upon the extent of heat treatment. The quality characteristics of the alloyed hot-dip galvanized steel sheet are significantly affected by the deposit amounts of the $\Gamma$ phase and $\zeta$ phase in the galvanized layer. Therefore, in order to produce the alloyed hot-dip galvanized steel sheet of high quality, it is important to control the heat treatment conditions, for example, the heating temperature or heating time, to constantly control the deposit amounts of the $\Gamma$ phase and $\zeta$ phase to appropriate levels.

Methods of measuring the deposit amounts of metal phases contained in a galvanized layer of an alloyed hot-dip galvanized steel sheet by X-ray diffractometry have been disclosed.

An example of the conventional methods is the method disclosed in Japanese Unexamined Patent Publication No. 9-33455. In this method, the galvanized layer is irradiated with X-rays to determine the deposit amounts of the $\Gamma$ phase and $\zeta$ phase of the alloyed hot-dip galvanized steel sheet by using the measured intensities of diffracted X-rays from the Fe—Zn alloy phases, the previously measured intensities of diffracted X-rays from an alloyed hot-dip galvanized steel sheet having known deposit amounts of the $\Gamma$ phase and $\zeta$ phase, and a theoretical intensity formula for diffracted X-rays, calculating the degree of alloying. By using the theoretical intensity formula for diffracted X-rays, the number of reference materials can be significantly decreased, as compared with a conventional method. However, the intensities of diffracted X-rays are the same as conventional values. Therefore, there is no resolution of the problem of deteriorating measurement accuracy when the obtained diffracted X-ray intensity is low.

On-line measurement of a running steel sheet, such as on-line measurement of a steel sheet in a surface treatment step, also has a problem in which accurate measurement is made impossible by the influence of vibration of the steel sheet. Namely, the distance between an X-ray diffraction position and a detection system varies with vibration of the steel sheet flowing on a line to influence the diffracted X-ray intensity. Since alloy phases having small deposit amounts, such as the $\Gamma$ phase and $\zeta$ phase, show low diffracted X-ray intensity, the deposit amounts of these phases cannot be easily evaluated with high accuracy.

In the use of diffracted X-rays for a galvanized layer containing a plurality of metal phases, the occurrence frequency of superposition of other peaks is increased to make quantitative accurate analysis more difficult.

The on-line measurement in the surface treatment step requires feedback of measurement results within a short time. In this case, the time of detection by a scintillation counter cannot be extended to fail to increase the count number of diffracted X-rays, and thus the above problems become significant.

Although, in the invention of Japanese Unexamined Patent Publication No. 9-33455, the above problems are solved by setting the appropriate theoretical intensity formula, the fundamental problem of week diffracted X-ray intensity cannot be resolved.

Another example of the conventional methods is the method disclosed in Japanese Unexamined Patent Publication No. 5-45305. This method is a method of measuring the degree of alloying of a galvanized layer in which the degree of alloying of the galvanized layer is measured by using a ratio between two specified X-ray diffraction intensities of alloy phases. Also, the degree of alloying of the galvanized layer is measured by using a ratio of one specified X-ray diffraction intensity of alloy phases to background intensity. This method is aimed at measuring the degree of alloying of the galvanized layer with high accuracy in a practical alloying region. However, the detected X-ray diffraction intensity itself is not increased. Therefore, sufficient accuracy cannot be obtained according to the conditions of a measurement sample.

The above publications respectively disclose drawings schematically showing parallel beam optical system X-ray diffractometers used for the conventional techniques. However, these diffractometers have no characteristic as an apparatus.

DISCLOSURE OF INVENTION

In consideration of the above-described circumstances, an object of the present invention is to increase diffracted X-ray intensity from a metal phase contained in a galvanized layer to improve the measurement accuracy of the deposit amount of the metal phase contained in the galvanized layer. Another object of the present invention is to contribute to the production of a galvanized product of high quality. A further object of the present invention is to provide a measuring apparatus and method capable of accurately measuring the deposit amount of an alloy phase even when the distance between an X-ray diffraction position and a detection system varies with vibration of a steel sheet, like in on-line measurement of a running steel sheet.

In order to improve the measurement accuracy of minor components by X-ray diffractometry, the inventors selected the method of increasing the detected X-ray diffraction intensity itself as a drastic measure. The detected X-ray diffraction intensity itself was increased to achieve a method and apparatus for accurately quantitatively determining minor components of the present invention. Particularly, the inventors invented a method and apparatus for acculately quantitatively determining the degree of alloying of a galvanized layer of a metal.

In order to increase the detected X-ray diffraction intensity itself, a detector capable of detecting larger quantities of diffracted X-rays than a conventional detector was designed. In another device, the parallelism of the produced X-rays is improved to decrease diverging X-rays, thereby increasing diffracted X-ray intensity, as compared with a conventional method. The present invention relates to these methods and an apparatus for realizing the methods, and a method of producing a galvanized steel sheet by using the methods and apparatus.

The present invention provides a method and apparatus for measuring the deposit amount of a metal phase contained in a galvanized layer by X-ray diffractometry, the method comprising measuring diffracted X-rays from the metal phase contained in the galvanized layer over a predetermined range on a Debye ring, and integrating the obtained X-ray diffraction intensity data to permit the accurate measurement of the deposit amount of the metal phase.

The present invention also provides a method of measuring the deposit amount of a metal phase contained in a galvanized layer by X-ray diffractometry, the method comprising measuring diffracted X-rays from the metal phase at a plurality of positions on at least one Debye ring formed by the diffracted X-rays to detect large quantities of X-rays, and integrating the obtained X-ray diffraction intensity data to increase the X-ray intensity data, thereby permitting the accurate measurement of the deposit amount of the metal phase.

As the metal phase, a single phase or a plurality of phases may be used, and when the metal phase is either a pure metal phase or an alloy phase, accurate measurement is possible. More specifically, the present invention is preferably applied to the case in which plating is hot-dip galvanization or alloying hot-dip galvanization.

Furthermore, the measuring method of the present invention can be performed in the step of treating the surface of a steel sheet to permit accurate on-line measurement of the deposit amount of the metal phase contained in the galvanized layer. The results of measurement can be used for controlling alloying conditions.

The present invention further provides an apparatus for measuring the deposit amount of a metal phase in a galvanized layer by using the above-described method, the apparatus comprising an X-ray source for irradiating the galvanized layer containing the metal phase with an X-ray beam, a detector for detecting diffracted X-rays from the metal phase contained in the galvanized layer over a predetermined range along a Debye ring, and a data processing device for processing data of the X-ray intensity detected by the detector. The detector has an X-ray detection surface curved along the Debye ring. The detector may be a scintillation counter having the function to scan the predetermined range along the Debye ring.

The present invention further provides an apparatus for measuring the deposit amount of a metal phase in a galvanized layer, comprising an X-ray source emitting an X-ray beam, a plurality of X-ray detectors disposed on at least one Debye ring of diffracted X-rays produced from a material irradiated with the X-rays, for detecting diffracted X-rays, and an integrating meter for integrating the diffracted X-ray intensity data obtained by the X-ray detectors for at least one Debye ring.

The present invention further provides an apparatus for measuring the deposit amount of an alloy phase in a galvanized layer on a steel sheet by using X-ray diffractometry, the apparatus comprising X-ray radiation means comprising an X-ray source emitting an X-ray beam, a multilayer film mirror for compressing the emitted X-rays and making the emitted X-rays monochromatic and parallel, and a slit for transmitting a portion of the parallel X-rays, and X-ray detection means for detecting diffracted X-rays from a measurement material contained in the galvanized layer on the surface of the steel sheet irradiated with the X-rays.

In the method of measuring the deposit amount of an alloy phase contained in a galvanized layer on a steel sheet by X-ray diffractometry, in X-ray irradiation of the measurement material contained in the galvanized layer on the surface of the steel sheet, the X-ray beam produced by the X-ray source is made parallel by using the multilayer film mirror to permit accurate measurement of the deposit amount of the alloy phase in the galvanized layer on the steel sheet.

In the method and apparatus of the present invention, the detected X-ray intensity (total amount of X-rays detected per unit time) can be increased to improve the accuracy of measurement of the deposit amount of the metal phase.

DISCLOSURE OF INVENTION

The present invention is described in further detail below with reference to the drawings. The present invention is not limited to embodiments.

First, an X-ray detector comprising a curved detection surface is described in detail.

In a method of measuring the deposit amount of a metal phase contained in a galvanized layer of the present invention, diffracted X-rays from the metal phase contained in the galvanized layer are measured over a predetermined range on a Debye ring to significantly increase the count number of diffracted X-rays per unit time in detection means. The obtained X-ray intensity data (the count number per unit time) is integrated for a predetermined time. By passing through these steps, the X-ray intensity data (integrated total amount) is significantly increased to improve the measurement accuracy of the deposit amount of the metal phase.

Like in measurement of a small amount of metal phase contained in a galvanized layer containing a plurality of metal phases, even when the relative intensity of diffracted X-rays of the metal phase to be measured is significantly weak, the measuring method of the present invention can accurately measure the deposit amount of the metal phase to be measured within a short time. This is particularly effective for a condition requiring feedback of measurement data within a short time, like in on-line measurement.

Figure 1:
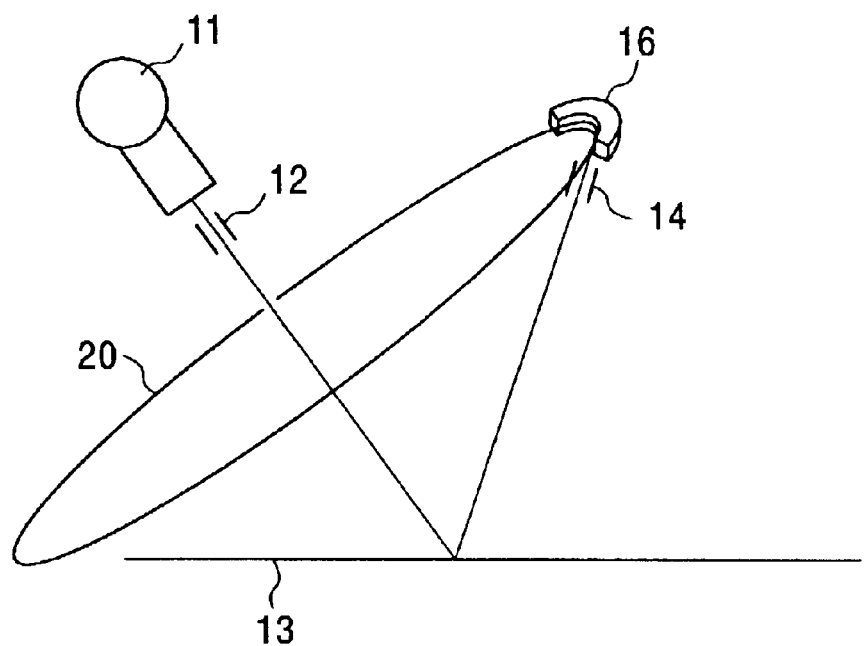
FIG. 1 is a drawing schematically showing the state in which X-rays emitted from an X-ray source are diffracted and then detected in the present invention.

FIG. 1 shows a relation in the measuring method of the present invention in which X-rays emitted from an X-ray source are diffracted and detected by detection means. In FIG. 1, X-rays emitted from an X-ray source 11 are incident on a surface 13 of a steel sheet through a slit 12 to produce diffracted X-rays by a metal phase (not shown in the drawing). The diffracted X-rays spread in a conical shape with an axis in the X-ray radiation direction. The bottom of the conical shape corresponds to a Debye ring 20. In the measuring method of the present invention, the diffracted X-rays are measured over a predetermined range on the Debye ring.

Figure 2:
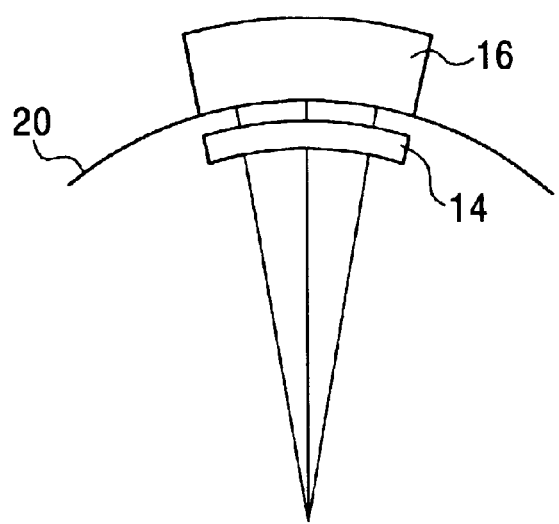
FIG. 2 is an enlarged partial view showing the diffracted X-ray detection means or detector shown in FIG. 1, which is disposed on a Debye ring, has a predetermined length, and is curved along the Debye ring according to the present invention.

FIG. 2 is an enlarged partial view showing the relation between the Debye ring and the detection means for diffracted X-rays shown in FIG. 1. As shown in FIG. 2, in the measuring method of the present invention, detection means 16 curved along the Debye ring is disposed on the Debye ring to detect the diffracted X-rays in the predetermined range on the Debye ring. Therefore, the count number of the measured diffracted X-rays per unit time is increased, and the obtained diffracted X-ray intensity data is integrated by a data processing device (not shown in the drawing) to increase the X-ray intensity data, thereby improving the measurement accuracy of the deposit amount of the metal phase.

Measurement of the X-rays over the predetermined range on the Debye ring is not limited to measurement with the X-ray detector curved along the Debye ring as shown in FIG. 2, and measurement may be performed by means for scanning an X-ray detector such as a scintillation counter or the like over a predetermined range in the direction of the Debye ring.

The predetermined range of diffracted X-ray measurement is appropriately selected. In measurement of a layer having a low deposit amount, a predetermined range is selected so as to obtain measured intensity enough to obtain sufficient detection accuracy.

The position of the predetermined range of diffracted X-ray detection on the Debye ring is not always limited. This is because a galvanized layer, particularly an alloyed hot-dip galvanized steel sheet, is polycrystalline, and thus the diffracted X-rays from a metal phase generally exhibit no useful orientation on the Debye ring. Therefore, the position of the detection means may be appropriately selected in consideration of arrangement of other components, and the like.

Figure 3:
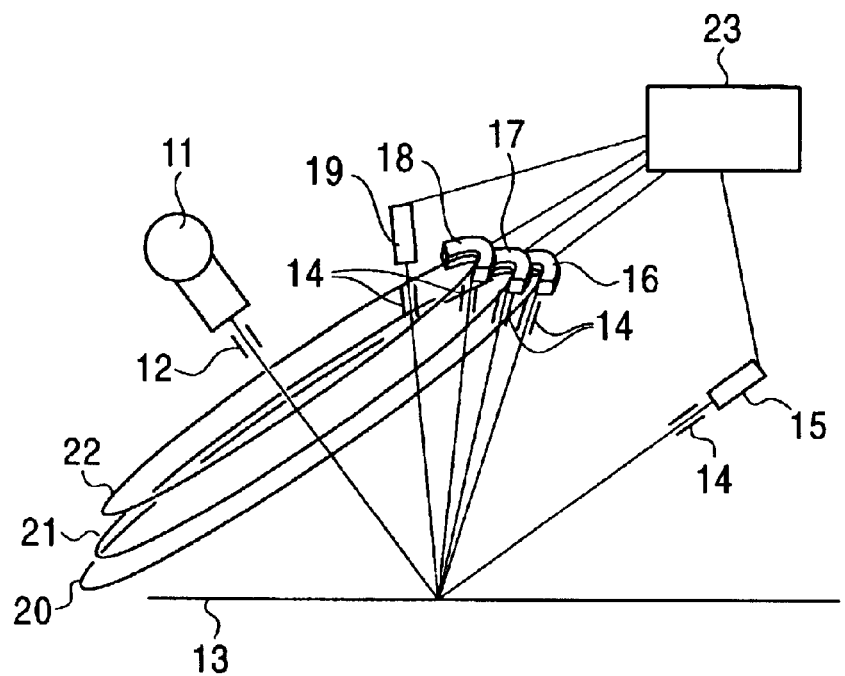
FIG. 3 is a conceptual diagram of an apparatus for measuring the deposit amount of a metal phase contained in a galvanized layer of the present invention, in which the deposit amounts of $\delta_1$ phase, $\zeta$ phase and $\Gamma$ phase of an alloyed hot-dip galvanized steel sheet are measured.
Figure 8:
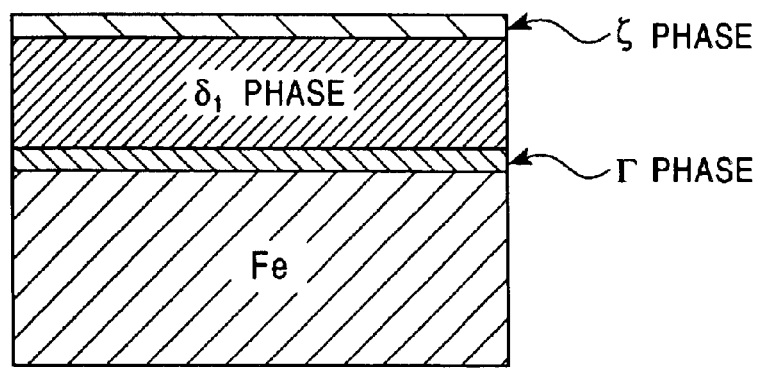
FIG. 8 is a schematic sectional view showing a galvanized layer of an alloyed hot-dip galvanized steel sheet, particularly a distribution of the $\delta_1$ phase, $\zeta$ phase and $\Gamma$ phase contained in the galvanized layer.

For a plurality of metal phases contained in the galvanized layer, diffracted X-ray detection means is arranged on the Debye ring corresponding to each of the metal phases to permit measurement of the deposit amounts of the plurality of metal phases. For example, an alloyed hot-dip galvanized layer contains three phases including the $\delta_1$ phase, $\zeta$ phase and $\Gamma$ phase, as show in FIG. 8, and thus means for detecting diffracted X-ray intensity is disposed for measuring intensity over a predetermined range on each of the Debye rings of diffracted X-rays of the three phases, thereby simultaneously obtaining the deposit amounts of the three phases. FIG. 3 is a conceptual diagram of a measuring apparatus for simultaneously measuring the deposit amounts of the $\delta_1$ phase, the $\zeta$ phase and the $\Gamma$ phase contained in the galvanized layer of the alloyed hot-dip galvanized steel sheet according to the present invention. X-rays emitted from an X-ray source 11 are incident on a surface 13 of the steel sheet through a slit 12 to produce diffracted X-rays respectively corresponding to the $\delta_1$ phase, the ' phase and the $\Gamma$ phase. The diffracted X-rays spread in a conical shape with an axis in the X-ray radiation direction to form the Debye rings 20, 21 and 22 respectively corresponding to the alloy phases.

Reference numerals 16 to 18 denote detection means for detecting diffracted X-rays over the predetermined ranges on the respective Debye rings, reference numeral 16 denoting a detector for the $\delta_1$ phase, reference numeral 17 denoting a detector for the $\zeta$ phase, and reference numeral 18 denoting a detector for the $\Gamma$ phase. The X-ray intensity data obtained by detection with these X-ray detectors is integrated by a data processing device 23 to accurately measure the deposit amount of each of the metal phases within a short time. Reference numerals 15 and 19 respectively denote scintillation counters for measuring a background element. In actual measurement, the Debye rings corresponding to the three phases are not always formed in the order shown in FIG. 3.

Although FIG. 3 shows the state in which diffracted X-rays are measured over the predetermined ranges on the Debye rings for all the $\delta_1$ phase, the $\zeta$ phase and the $\Gamma$ phase, the measuring method of the present invention may comprise measurement over the predetermined range on at least one Debye ring. The diffracted X-rays are not necessarily measured over the predetermined ranges on all Debye rings. The X-rays may be measured over the predetermined range in consideration of estimated diffracted X-ray intensity, or measured at a point on the Debye ring by a conventional method. For example, in the alloyed hot-dip galvanized steel sheet, for metal phases such as the $\zeta$ phase and the $\Gamma$ phase, which contained in small amounts in the galvanized layer, X-rays are measured over the predetermined ranges on the Debye rings in order to increase X-ray detection intensity, while for a metal phase such as the $\delta_1$ phase which is contained in a large amount in the galvanized layer, X-rays may be measured at a point on the Debye ring by the conventional method because diffracted X-ray intensity is stronger than other metal phases.

The predetermined ranges of X-ray measurement on all Debye rings are not always the same, and the predetermined ranges are appropriately selected according to estimated diffracted X-ray intensity. For example, in the alloyed hot-dip galvanized steel sheet, for the $\zeta$ phase and $\Gamma$ phase, which are contained in small amounts in the galvanized layer, the predetermined ranges are provided to be wider than that of the $\delta_1$ phase in order to further increase diffracted X-ray intensity.

A measuring apparatus of the present invention comprises an X-ray source radiating an X-ray beam, an X-ray detector for detecting the diffracted X-rays produced from a material irradiated with the X-rays in the predetermined range along the Debye ring, and a data processing device for processing the diffracted X-ray intensity data obtained from the X-ray detector.

The X-ray source comprises an X-ray generator generating an X-ray beam, and a slit for restricting divergence of the X-ray beam. In the present invention, an inclusion X-ray tube or rotating anticathode can be used as the X-ray generator. In either of the generators, with the high voltage of several tens kV applied between a filament and an anticathode, thermal electrons produced by supplying a current to the filament are accelerated at the high voltage to collide with a metal target, thereby producing X-rays.

The target is selected in consideration of X-ray absorption by a sample and measurement accuracy, and Cu, Cr, Fe, Co, Mo, and the like are used. In the measuring apparatus of the present invention, Cr, Fe and Co suitable for measurement of iron-based samples are preferred, and particularly Cr is preferred because of the excellent SN ratio.

The slit comprises a Soller slit for suppressing the longitudinal divergence of the X-ray beam, and a divergent slit for restricting the divergence angle in a horizontal plane for a sample.

The X-rays produced from the metal target of the X-ray tube contain desired Kα rays, as well as Kβ ray and white X-ray components, and thus these components must be removed to form a monochromatic beam. The X-ray beam is made monochromatic by inserting a Kβ filter comprising a metal foil in front of a light receiving slit, or using a monochrometer.

The diffracted rays produced by irradiating the surface of a material with the X-ray beam are converged through the light receiving slit, and measured by detection with the X-ray detector disposed on the Debye ring through the Soller slit and the divergence slit.

A typical example of the detector used in the apparatus of the present invention is a position-sensitive proportional detector. In this detector, an anode core wire and a cathode are arranged with a predetermined length, and a detector gas is passed at a high voltage to be ionized by incident X-rays to produce induced charge on the cathode so that the X-ray detection position and intensity can be measured by measuring the induced charge. At present, available position-sensitive proportional detectors are divided into a linear type and a curved type.

As described above, the position-sensitive proportional detector is a device capable of detecting and measuring X-rays over the predetermined range, and determining not only the detected X-ray intensity but also the detection position. However, when the linear-type position-sensitive proportional detector is used for the measuring apparatus of the present invention, there are the following problems. Since the linear-type position-sensitive proportional detector has a linear detection surface, the detection surface does not coincide with the shape of the Debye ring when the detector is disposed on the Debye ring. As a result, the distance between an irradiation position on a sample and the detection surface, i.e., the reachable range of the diffracted X-rays, varies to cause the need for correction in integration of the detected X-ray intensity data. Also, the curved type is originally intended for detection in the diffraction angle direction, and thus the detection surface does not coincide with the shape of the Debye ring. Therefore, like in the linear-type position-sensitive proportional detector, correction is required when it is disposed on the Debye ring. As a result of investigation of the above problems, it was found that when the detection surface (1) has a predetermined length, and (2) is curved along the Debye ring, a detector capable of detecting diffracted X-rays over the predetermined range on the Debye ring can be produced to obtain an X-ray detector necessary for the measuring apparatus of the present invention.

Accordingly, in a preferred embodiment of the present invention, the curved-type position-sensitive proportional detector is formed to have a predetermined length and to be curved along the Debye ring to be measured. Alternatively, an ordinary proportional counter may be curved to have a predetermined length. Furthermore, a film such as an imaging plate, in which a fine crystal of a photostimulable phosphor is coated on a flexible polymer surface, may be arranged to have a predetermined length and to be curved along the Debye ring so that X-rays are detected by the luminescence function of X-ray irradiation.

In the measuring apparatus of the present invention, the predetermined length of the detection surface of the X-ray detector is not limited, and the predetermined length is selected so as to produce measured intensity enough to obtain detection accuracy sufficient for measurement of a phase having a low deposit amount.

In the measuring apparatus of the present invention, the position on the Debye ring where the X-ray detection means is disposed is not limited, and the position may be appropriately selected. Particularly, in measurement of a polycrystalline surface such as the alloyed hot-dip galvanized layer, diffracted X-rays obtained by X-ray irradiation of the polycrystalline surface exhibit no useful orientation on the Debye ring, and thus the arrangement position of the detection means may be appropriately selected in consideration of the arrangement of other components in the apparatus, etc. On the other hand, like in X-ray irradiation of a single crystal surface, when diffracted X-ray intensity on the Debye ring has orientation, the detection means is disposed in consideration of the orientation.

In the measuring apparatus of the present invention, X-ray diffraction to be measured is not limited to one, and a plurality of X-ray diffractions may be measured. In this case, the X-ray detectors are not necessarily disposed for measuring X-rays over the predetermined lengths on all Debye rings. For example, in the alloyed hot-dip galvanized steel sheet, diffracted X-rays from the metal phases such as the ζ phase and Γ phase contained in the galvanized layer are detected with the detection means for detecting X-rays over the predetermined lengths, and the obtained X-ray intensity data is integrated by the data processing device described below to increase the X-ray intensity data. On the other hand, diffracted X-rays from the metal phase such as the $\delta_1$ phase contained in a large amount in the galvanized layer may be detected with ordinary X-ray detection means for detecting X-rays at a point.

The data processing device of the measuring apparatus of the present invention is not limited as long as the X-ray intensity obtained by the X-ray detection means can be integrated. The data processing device may be a device for each of a plurality of X-ray diffractions to be measured, or a device capable of integrating X-rays of all diffractions to be measured. An object material to be measured by the measuring apparatus of the present invention is not always limited to the deposit amount of a metal phase contained in the galvanized layer. For example, a trace component in a composition may be measured.

The present invention also provides a method of producing the alloyed hot-dip galvanized steel sheet by using the measuring method. In the producing method of the present invention, each of the metal phases contained in the galvanized layer is measured by an on-line method in the step of treating the surface of the steel sheet, and alloying conditions for the galvanized layer, i.e., the heat treatment conditions of the steel sheet, for example, the heating temperature and heating time, are controlled based on the obtained measurement results to control the deposit amount of each of the metal phases in the galvanized layer to an optimum condition, thereby producing the alloyed hot-dip galvanized steel sheet in which the deposit amount of each of the metal phases contained in the galvanized layer is optimized. In the hot-dip galvanized steel sheet after alloying in the step of treating the surface of the steel sheet at a line speed of 50 to 120 m/min, the deposit amounts of the $\delta_1$ phase, the $\Gamma$ phase and the $\zeta$ phase contained in the galvanized layer are preferably in the ranges of 20 to 114 g/m$^2$, 0 to 2 g/m$^2$ and 0 to 4 g/m$^2$, respectively.

EXAMPLE 1

The alloyed hot-dip galvanized steel sheet of the present invention will be in further detail below with reference to examples.

Of the metal phases of the $\delta_1$ phase, the $\zeta$ phase and $\Gamma$ phase contained in the galvanized layer of the alloyed hot-dip galvanized steel sheet, the $\zeta$ phase required to have highest deposit amount accuracy from the viewpoint of quality of a steel sheet product was selected as a measurement object. The variation width in deposit amount measurements required for the $\zeta$ phase in the steel sheet product was 0.37 g/m$^2$. The deposit amount measurements were obtained by converting the count numbers of diffracted X-rays into the deposit amounts based on standard data.

In the apparatus shown in FIG. 3, a Cr tube was used as the X-ray source, and X-rays (K$\alpha$ rays) were emitted with a tube voltage of 40 kV and a tube current of 70 mA. The diffraction peak of the $\zeta$ phase with a crystal plane distance d of 1.26 Å was measured as described below. First, as a comparative example, intensity was measured with a conventional scintillation counter disposed on the Debye ring. Next, intensity was measured by detection means having a detection surface curved along the Debye ring to measure the diffracted X-ray over the predetermined range on the Debye ring according to the present invention. As the detection means, a position-sensitive proportional detector having a detection surface with a length of 20 cm and a shape curved with the same curvature as the Debye ring was used.

In the comparative example using the scintillation counter for measurement at a point, the repeat accuracy was 4.0%, while in the use of the detecting method of the present invention, the repeat accuracy was 2.8%.

The repeat accuracy is represented by the following ordinary equation (1):

$$\text{(Repeat accuracy)} = \frac{\sqrt{\frac{\sum_{i=1}^{n}(x_i - x_a)^2}{n}}}{x_a} \times 100 \, (\%) \quad \text{Equation 1}$$

However, I represents ith measurement, n represents the total number of times of repeated measurements, $X_i$ represents ith diffracted X-ray intensity, and $X_a$ represents an average of diffracted X-ray intensities of n measurements.

In the comparative example, the accuracy of the deposit amount was 0.39 g/m$^2$, while in the example of the present invention, the deposit amount accuracy was 0.28 g/m$^2$. By using the method of the present invention, the repeat accuracy of measurement was improved to achieve the required accuracy of deposit amount measurement.

A detailed description will now be made of the case in which "a plurality of detectors are provided".

The X-rays from a metal phase contained in a galvanized layer were measured at a plurality of positions on one Debye ring, and the obtained diffracted X-ray intensity data was integrated to increase the X-ray intensity data, measuring the deposit amount of the metal phase. In this measuring method, X-ray detectors for detecting diffracted X-rays are arranged at a plurality of positions on the same Debye ring of diffracted X-rays from the metal phase to be measured.

Figure 4:
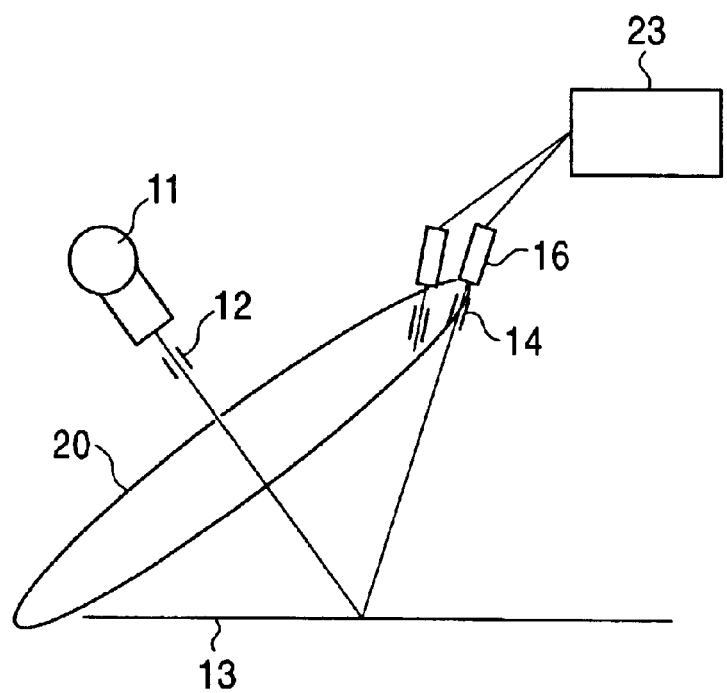
FIG. 4 is a conceptual diagram of a measuring method using a plurality of X-ray detectors according to the present invention.

FIG. 4 is a conceptual diagram of the measuring method of the present invention. In FIG. 4, X-rays emitted from an X-ray source 11 are incident on a surface 13 of a steel sheet through a slit 12 to produce diffracted X-rays from a metal phase (not shown in the drawing) contained in a galvanized layer. The diffracted X-rays spread in a conical shape with respect to the incidence direction of the emitted X-rays, and the bottom of the conical shape forms a Debye ring 20. In the present invention, a plurality of X-ray detectors 16 are arranged on the Debye ring to detect and measure diffracted X-rays through slits 14. The diffracted X-ray intensity data obtained by the plurality of X-ray detectors 16 is increased by integration by an integrating meter 23 to improve the measurement accuracy of the deposit amount of a metal phase.

Figure 5:
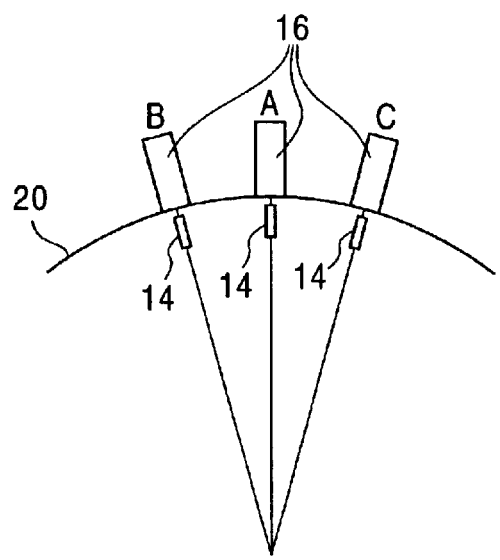
FIG. 5 is an enlarged partial view showing a measuring method of the present invention in which a plurality of X-ray detectors are disposed on the same Debye ring.

FIG. 5 is an enlarged partial view showing the state in which a plurality of X-ray detectors are arranged on the Debye ring. In FIG. 5, reference numeral 20 denotes the Debye ring, and reference numeral 16 denotes the X-ray detector arranged on the Debye ring Characters A to C represents a plurality of X-ray detectors disposed on the same Debye ring. The number and positions of the X-ray detectors disposed on the Debye ring are not limited to those shown in FIG. 5, and can be appropriately selected according to demand. However, in measuring a layer having a small deposit amount, a predetermined range is selected for obtaining measured intensity enough to obtain sufficient detection accuracy.

For example, like in the case in which the galvanized layer contains a plurality of metal phases, and the amount of the metal phase to be measured is very small, when many background components are contained, and the relative strength of desired diffracted X-rays is significantly low, the number of the X-ray detectors arranged on the Debye ring is appropriately increased. For example, for a Fe—Zn alloy phase, two or three scintillation counters each comprising a NaI (sodium iodide) and generally used as an X-ray detector are arranged.

The alloy phase of the galvanized layer, particularly the hot-dip galvanized steel sheet or alloyed hot-dip galvanized steel sheet, is polycrystalline, and the obtained diffracted X-ray intensity has no useful intensity distribution in the direction along the Debye ring. Namely, the intensity distribution is generally substantially uniform. In this case, the detectors may be arranged at any positions on the Debye ring Therefore, the X-ray detectors are arranged in consideration of the surrounding conditions such as the arrangement of other components, and the like.

Figure 6:
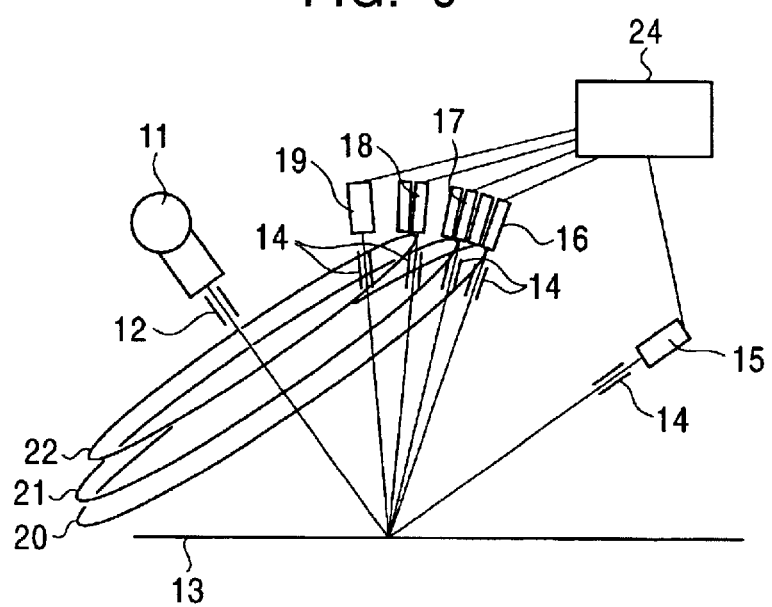
FIG. 6 is a conceptual diagram of a measuring apparatus of the present invention in which the deposit amounts of $\delta_1$ phase, $\zeta$ phase and $\Gamma$ phase of a galvanized layer of an alloyed hot-dip galvanized steel sheet are measured.

In the present invention, the metal phase to be measured is not limited to one, and a plurality of metal phases may be measured. For example, for the galvanized layer of the alloyed hot-dip galvanized steel sheet shown in FIG. 8, the deposit amounts of all of the Γ phase, the $\delta_1$ phase and the ζ phase can be simultaneously measured. FIG. 6 shows an example of the measuring apparatus for measuring the deposit amounts of the Γ phase, the $\delta_1$ phase and the ζ phase contained in the galvanized layer of the alloyed hot-dip galvanized steel sheet. X-rays emitted from an X-ray source 11 are incident on a surface 13 of the steel sheet through a slit 12 to produce diffracted X-rays respectively corresponding to the Γ phase, the $\delta_1$ phase and ζ phase. The diffracted X-rays spread in a conical shape with an axis in the X-ray radiation direction to form the Debye rings 20, 21 and 22 respectively corresponding to the alloy phases. Reference numerals 16 to 18 denote a plurality of X-ray detectors respectively arranged on the Debye rings. Reference numeral 16 denotes a scintillation counter for measuring the $\delta_1$ phase, reference numeral 17 denotes a scintillation counter for measuring the ζ phase, and reference numeral 18 denotes a scintillation counter for measuring the Γ phase. Reference numerals 15 and 19 respectively denote scintillation counters for measuring a background element. The X-ray intensity data obtained by detection with these scintillation counters is integrated by a data processing device 24 to measure the deposit amount of each of the metal phases. Although, in FIG. 6, a plurality of X-ray detectors are provided for all the Γ phase, $\delta_1$ phase and ζ phase, the measuring method of the present invention may comprise measurement at a plurality of positions on at least one Debye ring, and a plurality of X-ray detectors are not necessarily arranged on each of all Debye rings. It is possible to appropriately select the arrangement of a plurality of X-ray detectors or a single X-ray detector in consideration of estimated diffracted X-ray intensity. For example, in the alloyed hot-dip galvanized steel sheet, for metal phases such as the ζ phase and Γ phase, which contained in small amounts in the galvanized layer, X-rays are measured at a plurality of positions on the Debye rings in order to increase X-ray detection intensity, while for a metal phase such as the $\delta_1$ phase which is contained in a large amount in the galvanized layer, X-rays may be measured at a point on the Debye ring because diffracted X-ray intensity is stronger than other metal phases.

The measuring method of the present may be performed by an on-line method in the step of treating the surface of a steel sheet. The measuring method of the present invention can measure the deposit amount of a metal phase with high accuracy within a short time. Therefore, the deposit amount can be measured in the step of treating the surface of a steel sheet, and the results of measurement can be fed back to the surface treatment step to permit an attempt to optimize the deposit amount of the metal phase contained in the galvanized layer.

A measuring apparatus of the present invention comprises an X-ray source radiating an X-ray beam, a plurality of X-ray detectors disposed on at lest one Debye ring of the diffracted X-rays produced from a material irradiated with the X-rays, for detecting diffracted X-rays, and an integrating meter for integrating the diffracted X-ray intensity data obtained from the X-ray detectors for the same Debye ring.

Like in the case in which the curved detection surface is provided, the X-ray source comprises an X-ray generator generating an X-ray beam, and a slit for restricting divergence of the X-ray beam. The X-ray generator, the target, the slit, means for making X-rays monochromatic, and diffraction X-ray guide to the detectors, which can be used in the present invention, are the same as the above-described case in which the curved detection surface is provided.

X-ray detectors which can be used for the apparatus of the present invention include a scintillation counter, a proportional counter, and a semiconductor detector, and the scintillation counter among these detectors is most general.

In the apparatus of the present invention, a plurality of X-ray detectors are disposed for the same Debye ring of at least one diffracted X-ray.

The number and positions of the X-ray detectors disposed on the Debye ring are not limited, and can be appropriately selected according to demand. For example, when it is estimated that many background components are contained, and diffracted X-ray intensity to be measured is low, the number of the X-ray detectors is appropriately increased. Like in the case in which a single crystal plane is irradiated with X-rays, when diffracted X-ray intensity on the Debye ring has orientation, the detectors are arranged in consideration of the orientation. When the detectors are arranged on each of the Debye rings of at least two diffracted X-rays, a plurality of detectors are not necessarily arranged on each of all Debye rings. For example, in the hot-dip galvanized layer or the alloyed hot-dip galvanized layer, for the Debye rings of weak diffracted X-rays from phases such as the ζ phase and Γ phase, which contained in small amounts, a plurality of X-ray detectors are arranged in order to increase X-ray intensity, while for the Debye ring of strong diffracted X-rays from a phase such as the $\delta_1$ phase which is contained in a large amount, a single X-ray detector may be disposed.

The integrating meter for integrating the diffracted X-ray intensity data obtained from the X-ray detectors arranged on the same Debye ring is not limited as long as the X-ray intensity data can be integrated. For example, an integrating meter for integrating the count value obtained by the scintillation counter can be used.

Although the integrating meter may be provided for each of the Debye rings, a data processing device may be provided, in which the X-ray intensity data obtained from the X-ray detectors disposed on all Debye rings is integrated for the same Debye ring, and a measurement obtained by the X-ray detector for measuring background is subtracted from the resultant integration value to output a measurement result.

In another aspect of the present invention, a method of producing an alloyed hot-dip galvanized steel sheet uses the above-described measuring method of the present invention. In the producing method of the present invention, the metal phases contained in the galvanized layer are measured by an on-line method in the step of treating the surface of the steel sheet to permit the production of the optimum alloyed hot-dip galvanized steel sheet, like in the application to the case in which the curved detection surface is provided. Like in the application to the case in which the curved detection surface is provided, in the alloyed hot-dip galvanized steel sheet after alloying in the step of treating the surface of the steel sheet at a line speed 50 to 120 m/min, the deposit amounts of the ζ phase, the Γ phase and the (phase contained in the galvanized layer are preferably controlled in the ranges of 20 to 114 g/m$^2$, 0 to 2 g/m$^2$ and 0 to 4 g/m$^2$, respectively.

EXAMPLE 2

Like in the case in which the curved detection surface was provided, the ζ phase was measured. A Cr tube was used as the X-ray source, and X-rays (Kα rays) were emitted with a tube voltage of 40 kV and a tube current of 70 mA. The diffraction peak of the ζ phase with a crystal plane distance d of 1.26 Å was measured by using an apparatus capable of measuring X-rays at two positions on the Debye ring of the ζ phase. First, as a comparative example, intensity was measured with a scintillation counter. Next, intensity was measured with two scintillation counters as an example of the present invention.

As a result, with the scintillation counter, the repeat accuracy was 4.0% (Comparative Example), while with the two scintillation counters according to the present invention, the repeat accuracy was 3.4% (Example). The repeat accuracy was defined as the same as Example 1.

The detection limit of accuracy of the deposit amount of the ζ phase was 0.39 g/m$^2$ (Comparative Example) and 0.34 g/m$^2$ (Example). In the present invention using the two scintillation counters, therefore, the repeat accuracy of measurement of the deposit amount of the ζ phase can be improved to achieve required measurement accuracy of the deposit amount.

A detail description will now be made of the case in which a multiplayer film mirror is provided.

The inventors conducted various studies of a measuring apparatus and method capable of precisely measuring the deposit amount of an alloy phase contained in a galvanized layer on a steel sheet even when the distance between a diffraction position and a detection system varies with vibration of the steel sheet. As a result, it was recognized that the problem of the conventional technique can be solved by irradiating the galvanized layer of the steel sheet with parallel X-rays, and measuring the diffracted X-rays from the measured material contained in the galvanized layer.

A measuring apparatus of the present invention, i.e., an apparatus for measuring the deposit amount of an alloy phase in a galvanized layer on a steel sheet, comprises X-ray radiation means comprising an X-ray source emitting an X-ray beam, means for compressing the emitted X-rays and making the X-rays parallel and monochromatic, for example, a multiplayer mirror (for example, Advance in X-ray Analysis, 31 (2000) 11–27), for compressing the emitted X-rays and making the X-rays parallel and monochromatic, and a slit transmitting a part of the parallel X-rays, and X-ray detection means for detecting the diffracted X-rays produced from a measured material in the galvanized layer on the surface of the steel sheet irradiated with the X-rays.

In the measuring apparatus of the present invention, the X-ray source comprises an X-ray generator generating an X-ray beam. In the measuring apparatus of the present invention, an inclusion X-ray tube or rotating anticathode can be used as the X-ray generator. In either of the generators, with the high voltage of several tens kV applied between a filament and a metal anticathode, thermal electrons produced by supplying a current to the filament are accelerated at the high voltage to collide with a metal target, thereby producing X-rays. The target is selected in consideration of X-ray absorption by a sample and measurement accuracy, and Cu, Cr, Fe, Co, Mo, and the like are used. In the measuring apparatus of the present invention, Cr, Fe and Co suitable for measurement of iron-based samples are preferred, and particularly Cr is preferred because of the excellent SN ratio.

In the measuring apparatus of the present invention, the multilayer film mirror is formed by periodically alternately laminated a heavy element and a light element to produce Bragg reflection so that the emitted X-rays can be compressed and made parallel and monochromatic.

In the measuring apparatus of the present invention, the X-ray beam emitted from the X-ray source is incident on the multilayer film mirror to be compressed and made parallel and monochromatic. As described above, the X-ray beam is made parallel, and the diffracted X-rays produced by X-ray beam irradiation of the material contained in the galvanized layer on the steel sheet surface as a sample are consequently made parallel. Therefore, even when the distance between the X-ray diffraction position and the detection system varies with vibration of the steel sheet, intensity of the detected diffracted X-rays is stable to improve the measurement accuracy of the deposit amount of a plating.

The multilayer film mirror has the effect of improving the resolution of diffraction peaks by making the X-rays monochromatic. Since the multilayer film mirror makes the X-ray beam more parallel than conventional so-called parallel X-rays, the X-ray components which are cut by a conventional slit contribute to irradiation of a sample surface, thereby improving the intensity of diffracted X-rays reaching a detector, as compared with the case using no multilayer film mirror. The improvements in resolution and diffraction intensity contribute to an improvement in measurement accuracy of the plating deposit amount.

The surface of a sample is irradiated with the X-ray beam made parallel and monochromatic and compressed by the multilayer film mirror to produce diffracted X-rays. The diffracted X-rays are detected and measured by an X-ray detector arranged on the Debye ring through a slit (Soller slit or divergence slit).

In the measuring apparatus of the present invention, the slit 12 prevents divergence of the X-ray beam produced by the X-ray source, and a Soller slit for suppressing divergence of the X-ray beam in the longitudinal direction, and a divergence slit for limiting the divergence angle of the sample in a horizontal plane can be used. The slit 12 preferably includes both of the slits.

X-ray detectors which can be used for the measuring apparatus of the present invention include a scintillation counter, a proportional counter, and a semiconductor detector, and the scintillation counter among these detectors is most general.

In the measuring apparatus of the present invention, the number of the X-ray detectors used is not limited. For example, in measurement of a plurality of phases, a number of X-ray detectors corresponding to the number of phases to be measured may be used.

The measuring apparatus of the present invention preferably comprises a data processing device for integrating the diffraction intensity data obtained by the X-ray detectors. In this case, the diffracted X-rays of a small amount of alloy phase having low diffraction intensity can be increased by integration. Therefore, the measuring method is advantageous for measurement of the deposit amounts of small amount of alloy phases, for example, the Γ phase and the ζ phase in the galvanized layer of the alloyed hot-dip galvanized steel sheet. As described above, when a plurality of X-ray detectors are used, the data processing device is capable of processing data of the plurality of X-ray detectors.

In a further aspect of the present invention, the method of measuring the deposit amount of an alloy phase in the galvanized layer on a steel sheet uses the above-descried apparatus of the present invention.

The measuring method of the present invention comprises irradiating a measurement material in the galvanized layer on the surface of the steel sheet with X-rays made parallel by the multilayer film mirror, and detecting the diffracted X-rays produced from the measurement material to measure the deposit amount of an alloy phase in the galvanized layer on the surface of the steel sheet. In the measuring method of the present invention, the galvanized layer is irradiated with the parallel X-rays, thereby greatly relieving the geometrical limit for obtaining diffraction intensity like in a concentration method. Namely, even when the distance between the X-ray diffraction position and the detection system varies with vibration of the running steel sheet, diffracted X-ray intensity is stabilized to permit the measurement of the deposit amount of an alloy phase contained in the plated. This is preferred for on-line measurement of the deposit amount of an alloy phase in the galvanized layer in the step of treating a surface of the alloyed hot-dip galvanized steel sheet. Namely, for the $\Gamma$ phase and the $\zeta$ phase in the galvanized layer, which significantly influence the quality properties of the galvanized layer due to only small variations in the deposit amounts, the deposit amounts can be measured with high accuracy by an on-line method. Therefore, the measurement results can be fed back to the surface treatment step to permit the production of the galvanized layer containing an alloy phase having a deposit amount in an optimum range.

EXAMPLE 3

A further detailed description will now be made of an apparatus for measuring the deposit amount of a Fe—Zn alloy phase of an alloyed hot-dip galvanized steel sheet using the measuring apparatus of the present invention as an example of the measuring apparatus of the first embodiment of the present invention with reference to the drawings. However, the measuring apparatus of the present invention is not limited to this.

Figure 7:
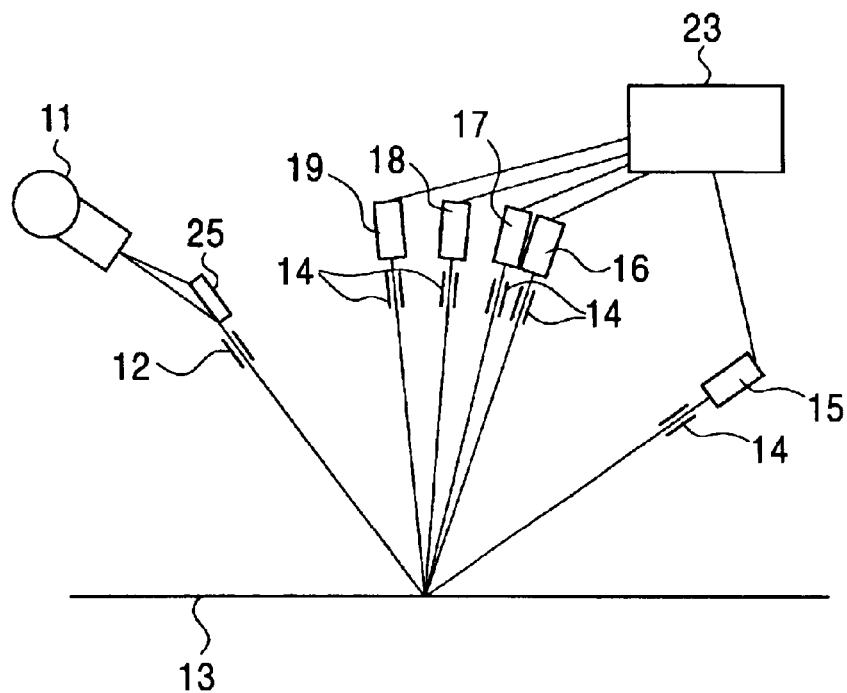
FIG. 7 is a conceptual diagram of an on-line measuring apparatus for measuring Fe-An alloy phases of an alloyed hot-dip galvanized steel sheet by using X-ray diffractometry.

FIG. 7 is a conceptual diagram of an on-line apparatus for measuring the deposit amount of a Fe—Zn alloy phase of an alloyed hot-dip galvanized steel sheet using the measuring apparatus of the present invention. In FIG. 7, reference numeral 11 denotes an X-ray source, reference numeral 25 denotes a multilayer film mirror, reference numerals 12 and 14 each denote a slit, reference numeral 13 denotes an alloyed hot-dip galvanized steel sheet, reference numerals 15 to 19 each denote a scintillation counter. Reference numerals 15 and 19 each denote the scintillation counter for measuring a background, and reference numerals 16, 17 and 18 denote the scintillation counters for measuring the $\delta_1$ phase, the $\zeta$ phase and $\Gamma$ phase, respectively. Reference numeral 23 denotes a data processing device.

In FIG. 7, the X-rays generated from the X-ray source 11 are compressed and made parallel and monochromatic by the multilayer film mirror 25, and incidence on the galvanized steel sheet 13 through the slit 12. The intensities of the diffracted X-rays are measured by the scintillation counters 15 to 19, and the deposit amounts of the $\zeta$ phase, the $\delta_1$ phase, and $\Gamma$ phase are accurately calculated by the data processing device 23.

In this example, a Cr tube was used as the X-ray source, and X-rays (K$\alpha$ rays) were emitted with a tube voltage of 40 kV and a tube current of 70 mA. The diffraction peaks of the $\zeta$ phase, the $\delta_1$ phase, and $\Gamma$ phase were measured with crystal plane distances d of 1.26 Å, 1.28 Å and 1.22 Å, respectively.

In this example, the deposit amount of the Fe—Zn alloy phase of the alloyed hot-dip galvanized steel sheet, which flowed at a traveling speed of 50 to 120 m/min on a continuous hot-dip galvanization line having an alloying apparatus, was measured by the apparatus (example) of the present invention comprising the multilayer film mirror 25, and an apparatus (comparative example) without the multilayer film mirror 25. In this example, of the $\delta_1$ phase, the $\zeta$ phase, and $\Gamma$ phase contained in the alloyed hot-dip galvanized steel sheet, the $\zeta$ phase required to have highest deposit amount accuracy from the viewpoint of quality of a steel sheet product was measured. The variation width (deposit amount accuracy) in deposit amount measurements required for the $\zeta$ phase in a steel sheet product was 0.37 g/m$^2$. The deposit amount measurements were obtained by converting the count numbers of diffracted X-rays into the deposit amounts based on standard data. The repeat accuracy is represented by the above-described equation (1).

The accuracies of the deposit amount of the $\zeta$ phase were 0.39 g/m$^2$ and 0.26 g/m$^2$. It was thus recognized that by using the method of the present invention, the repeat accuracy of measurement was improved to achieve the required accuracy of deposit amount measurement.

INDUSTRIAL APPLICABILITY

As described above, the method of the present invention produces high diffracted X-ray intensity from a metal phase to improve the measurement accuracy of a metal phase contained in a galvanized layer, particularly a metal phase contained in a small amount in the galvanized layer. Particularly, the present invention is effective for a case such as on-line measurement in the step of treating a surface of a steel sheet, in which the measurement results must be obtained within a short time. Furthermore, the method of producing a hot-dip galvanized steel sheet or an alloyed hot-dip galvanized steel sheet using the measuring method of the present invention is capable of feeding back the measurement results of the despot of a metal phase with high accuracy to the production process within a short time, thereby contributing the production of a high-quality galvanized steel sheet. Particularly, the present invention greatly contributes to stabilization of quality of an alloyed hot-dip galvanized steel sheet whose quality is significantly affected by small variations in the deposit amounts of the $\zeta$ phase and $\Gamma$ phase contained in small amounts in the galvanized layer.

Also, the measuring apparatus of the present invention is generally suitable for detecting and measuring trace components in a composition. An object to be measured by the method of the present invention is not limited to this, and the method can be widely used for measuring deposit amounts of metal phases contained in a galvanized layer.

What is claimed is:

1. A method of measuring the deposit amount of a metal phase contained in a galvanized layer by using X-ray diffractometry, the method comprising measuring diffracted X-rays from the metal phase contained in the galvanized layer over a predetermined range on a Debye ring, and integrating the obtained X-ray diffraction intensity data, wherein, prior to the step of measuring the diffracted X-rays, the method comprises a further step of limiting the diffracted X-rays being measured to those diffracted X-rays passing through a slit corresponding to a portion of a circumference of the Debye ring.

2. A method of measuring the deposit amount of a metal phase contained in a galvanized layer according to claim 1, wherein the metal phase is an alloy phase.

3. A method of measuring the deposit amount of a metal phase contained in a galvanized layer according to claim 1, wherein the metal phase comprises two phases or more.

4. A method of measuring the deposit amount of a metal phase contained in a galvanized layer according to claim 3, wherein the deposit amount of not less than one phase among the two phases or more is measured.

5. A method of measuring the deposit amount of a metal phase contained in a galvanized layer according to claim 1, wherein plating is hot-dip galvanization or alloying hot-dip galvanization.

6. A method of measuring the deposit amount of a metal phase contained in a galvanized layer according to claim 1, wherein measurement is performed in the step of treating a surface of a steel sheet.

7. A method of producing an alloyed hot-dip galvanized steel sheet comprising measuring the deposit amount of a metal phase contained in a galvanized layer by the measuring method according to claim 1, and controlling an alloying condition by using the result of measurement.

8. A method of measuring the deposit amount of a metal phase contained in a galvanized layer by using X-ray diffractometry, the method comprising measuring diffracted X-rays from the metal phase contained in the galvanized layer over a predetermined range on a Debye ring, and integrating the obtained X-ray diffraction intensity data, wherein, in the step of measuring the diffracted X-rays, a detector is shaped and positioned to limit the measured diffracted X-rays to X-rays diffracted into a predetermined circumferential portion of the Debye ring, the detector being shaped to have a detection surface matching the predetermined circumferential portion of the Debye ring.

* * * * *